United States Patent [19]

Kaschek et al.

[11] Patent Number: 5,219,557
[45] Date of Patent: Jun. 15, 1993

[54] COVERING AGENT FOR MICROSCOPY SPECIMENS

[75] Inventors: Renate Kaschek, Reinheim; Erwin Rieke, Seeheim, both of Fed. Rep. of Germany

[73] Assignee: Merck Patent Gesellschaft Mit Beschrankter Haftung, Darmstadt, Fed. Rep. of Germany

[21] Appl. No.: 137,031

[22] Filed: Dec. 23, 1987

[30] Foreign Application Priority Data

Dec. 24, 1986 [DE] Fed. Rep. of Germany ....... 3644467

[51] Int. Cl.$^5$ .......................... C09D 5/02; G01N 1/28; G01N 33/48; G02B 21/34
[52] U.S. Cl. ........................................ 424/3; 422/55; 422/57; 422/58; 436/166; 524/516; 524/512
[58] Field of Search ...................... 424/3; 524/516, 512

[56] References Cited

U.S. PATENT DOCUMENTS 4,302,480 11/1981 Fischer et al. ........................... 427/2

Primary Examiner—A. Lionel Clingman
Attorney, Agent, or Firm—Millen, White, Zelano & Branigan

[57] ABSTRACT

An aqueous covering agent containing a water-soluble base polymer and a further polymer for neutralizing the aqueous solution of the base polymer is provided for the sealing of microscopy specimens. The aqueous covering agent maintains the coloring of the specimens by staining techniques for prolonged periods of time.

5 Claims, No Drawings

COVERING AGENT FOR MICROSCOPY SPECIMENS

BACKGROUND OF THE INVENTION

The invention relates to a new covering agent for sealing microscopy specimens.

Covering agents for sealing microscopy specimens are known and are in use in histology and cytology. Cytochemical and immuno-histochemical preparations are usually first mounted on a microscope slide, fixed if required and/or stained by special methods for the better differentiation of intracellular constituents. They are then sealed with a covering agent. Alternatively, it is possible to carry out staining and sealing at the same time (German Auslegeschriften 2,635,438 and 2,635,449 and German Offenlegungsschrift 2,737,845).

Covering histochemical and cytochemical specimens requires the use of aqueous covering agents, since certain color-bearing substances are dissolved when organic solvents are used, whereby the staining of the specimens is destroyed.

Aqueous covering agents are known. They are based on water-soluble organic polymers, such as gelatin, polyvinylpyrrolidone or polyvinyl alcohol. The covering agents used hitherto are not satisfactory for various reasons. Covering agents containing gelatin must, for example, be liquefied by warming before being used.

If synthetic polymers are used as the base polymer, a customary acid or base is added to the aqueous polymer solution for the neutralization which is required. An example of a customary base is sodium hydroxide solution or aqueous ammonia solution.

Although covering agents of this type retain in part the specific staining of the cytochemical process, the counter-staining of the cell nucleus obtained with hemalum fades very rapidly.

If, for example, in order to detect the peroxidase reaction in leucocytes, the fixed and stained smears of blood or bone marrow are covered with glycerol gelatin or with a covering agent based on polyvinyl alcohol, after 3 weeks the nuclear staining has faded and the peroxidase staining has disappeared. Without a covering agent the black-brown granules in peroxidase-positive cells are stable for approximately 3 days, and, when covered with immersion oil, are stable even for only a few hours.

If a fixed and stained smear of blood or bone marrow intended to detect the 1-naphthyl-acetate esterase reaction in leucocytes is covered with glycerol gelatin, after 3 weeks the nuclear staining has faded. Without covering, the red-brown granules in esterase-positive cells are stable for approximately 5 days, or for only a few hours when directly covered with immersion oil.

Problems also arise in covering immuno-histochemically stained specimens with respect to retention of color. A process used for the detection of immunoglobulin G in a tonsil section is, for example, rendering peroxidase visible by incubation with 3-amino-9-ethyl-carbazole. Here, too, the nuclear staining fades in the course of a few weeks after being covered with glycerol gelatin. In addition, a considerable formation of bubbles is observed in the specimen.

It is as yet not known to obtain an aqueous covering agent for microscopy specimens which is capable of indicating colorations in intracellular constituents for a substantially longer time than in the above examples.

SUMMARY OF THE INVENTION

An object of this invention is to provide a new covering agent which can seal microscopy specimens and maintain for a prolonged period the colorations previously carried out for the better differentiation of the cell constituents.

Upon further study of the specification and appended claims, further objects and advantages of this invention will become apparent to those skilled in the art.

These objects have been achieved by an aqueous covering agent, based on water-soluble organic polymers, which is excellently suitable for maintaining the staining of microscopy specimens if a further polymer is used for the necessary neutralization of the aqueous solution of the polymer.

The invention, therefore, relates to an aqueous covering agent based on water-soluble organic polymers, for sealing microscopy specimens, which contains a further polymer by means of which the necessary neutralization has been achieved. In a particular embodiment, the further polymer employed is a basic polymer.

Finally, the invention relates to the use of such covering agents for sealing microscopy specimens.

The base polymer present in the covering agent according to the invention can be a polymer which is known to those skilled in the art and customarily used hitherto for this purpose; the organic base polymer present is preferably polyvinylpyrrolidone. In the case of polyvinylpyrrolidone, the molecular weight of the polymer is about 10,000–100,000 daltons, preferably about 10,000–50,000 daltons.

In an aqueous solution, the polymer concentration of the polyvinylpyrrolidone should be about 15–60% by weight, preferably about 20–40% by weight. Below about 15% by weight no permanent hardening takes place; above about 60% by weight a troublesome formation of bubbles is observed after complete hardening.

Polymeric acids and bases are employed to neutralize the polymer solution. Of the large number of polymers known to those skilled in the art and also commercially available, suitable polymers are those which dissolve readily in water. Bases which can be used in the case of polyvinylpyrrolidone are, for example, polyethyleneimine, poly-(trimethylolmelamine) and poly-(2-vinylpyridine), preferably polyethyleneimine having a molecular weight of about 500–10,000 daltons, preferably about 2,000 daltons.

The pH achieved by means of the polymeric base is about 6.5–7.5, preferably about 7.0. The amount of polymeric base to be added depends on the basicity and the acidity of the polymer solution. The covering agent can also contain the customary antimycotic agents, such as, for example, ethylene glycol monophenyl ether. The mixture suitable for use can be stored without limit, with the retention of its covering capacity, at about room temperature in a closed vessel.

A process for sealing microscopy specimens is carried out, for example, as follows:

The specimen, a smear of blood or bone marrow, is mounted on a slide and is fixed and stained by known processes. The covering agent is then applied to the specimen and is covered with a cover slip, whereby the covering agent surrounds the specimen and bonds the slide together with the specimen to the cover slip. Hardening at room temperature takes between 30 and 60 minutes using the covering agent according to the invention, whereas if other covering agents are used at least twice this time is required. Bubble-free microscopy specimens of excellent quality in which the cytochemical and histochemical stains and the cell nucleus counter-staining are highly stable over a period of at least 12 months are obtained after hardening.

The covering agent according to the invention thus makes it possible to prepare, in an advantageous manner, microscopy specimens which are permanently sealed, and the staining carried out for the better differentiation of different cell compartments being retained, surprisingly, for a long period.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

If a polymeric acid is used for neutralizing, the pH obtained is also about 6.5–7.5, preferably about 7.0.

All aspects of the covering agent are conventional unless indicated otherwise herein.

EXAMPLES

Preparation of a preferred covering agent.

EXAMPLE 1

1 kg of polyvinylpyrrolidone (MW 25,000) is dissolved in 2 kg of water and is then neutralized by adding approximately 25 g of polyethyleneimine (MW 2,000). After being filtered, the slightly yellowish solution is ready for use.

EXAMPLE 2

40 g of polyvinylpyrrolidone are dissolved in 100 g of water and are then neutralized by adding 4.5 g of poly-(trimethylolmelamine) (pH=6.8). After being filtered, the slightly yellowish solution is ready for use.

EXAMPLE 3

Detection of the peroxidase reaction in leucocytes.

The fixed smears of blood or bone marrow are stained in a 25% alcoholic solution of 4-chloro-1-naphthol and hydrogen peroxide. Subsequent nuclear staining is carried out with hemalum solution.

Without covering, the black-brown granules in peroxidase-positive cells are stable for approximately 3 days, or for only a few hours if directly covered with immersion oil.

If, on the other hand, covering is carried out using the covering agent according to the invention and a cover slip, the stain remains stable for at least 12 months.

If covering is carried out with glycerol gelatin or with a covering agent based on polyvinyl alcohol, after 3 weeks the nuclear staining has faded and the peroxidase staining has disappeared.

EXAMPLE 4

Detection of the 1-naphthyl-acetate esterase reaction in leucocytes.

The fixed smears of blood or bone marrow are stained in a buffered solution containing 1-naphthyl acetate and a diazonium salt. The subsequent nuclear staining is carried out by means of hemalum solution.

Without covering, the red-brown granules in esterase-positive cells are stable for approximately 5 days, or for only a few hours if directly covered with immersion oil.

If, on the other hand, covering is carried out using the covering agent according to the invention and a cover slip, the staining remains stable for at least 12 months.

If covering is carried out using glycerol gelatin, the nuclear staining has faded after 3 weeks.

EXAMPLE 5

Covering an immuno-histochemically stained specimen.

In order to detect immune globulin G in a tonsil section, the specimen was incubated by known processes with a primary antibody, a bridge antibody and a peroxidase/anti-peroxidase complex. The peroxidase was then rendered visible by incubation with 3-amino-9-ethylcarbazole. After counter-staining with hemalum solution, covering was carried out using the covering agent according to the invention. The staining remained stable for at least 12 months using this covering agent; after covering with glycerol gelatin, the nuclear staining faded in the course of a few weeks. In addition, considerable formation of bubbles within the specimen was noted in this case.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In an aqueous covering agent for sealing microscopy specimens, said covering agent comprising a water-soluble polyvinylpyrrolidone polymer, the improvement wherein said covering agent further comprises an amount of an additional polymer effective for substantially neutralizing said covering agent, said additional polymer being a basic polymer selected from the group consisting of polyethyleneimine, poly-(trimethylolmelamine), poly-(2-vinylpyridine), or mixtures thereof.

2. An aqueous covering agent according to claim 1, wherein after addition of said basic polymer, said covering agent has a pH of about 6.5–7.5.

3. The aqueous covering agent according to claim 1, wherein said covering agent has a concentration of polyvinylpyrrolidone of about 15–60% by weight.

4. An aqueous covering agent according to claim 1, further comprising an antimycotic agent.

5. A method for increasing the storage stability of an aqueous covering agent for sealing microscopy specimens, said covering agent comprising a water-soluble polyvinylpyrrolidone polymer, said process comprising:

adding to said aqueous covering agent an amount of an additional basic polymer effective to substantially neutralize said aqueous covering agent, said basic polymer being selected from the group consisting of polyethyleneimine, poly-(trimethylolmelamine), poly-(2-vinylpyridine), or mixtures thereof.

* * * * *